United States Patent
Biber et al.

(10) Patent No.: US 9,817,092 B2
(45) Date of Patent: Nov. 14, 2017

(54) METHOD AND MAGNETIC RESONANCE APPARATUS WITH A COOLING SYSTEM TO COOL A SUPERCONDUCTING BASIC MAGNETIC FIELD COIL

(71) Applicant: Siemens Aktiengesellschaft, Munich (DE)

(72) Inventors: Stephan Biber, Erlangen (DE); Thorsten Speckner, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 92 days.

(21) Appl. No.: 14/273,806

(22) Filed: May 9, 2014

(65) Prior Publication Data

US 2015/0346296 A1 Dec. 3, 2015

(30) Foreign Application Priority Data

May 10, 2013 (DE) .......................... 10 2013 208 631

(51) Int. Cl.
*G01R 33/38* (2006.01)
*H01F 6/06* (2006.01)
*G01R 33/3815* (2006.01)
*H01F 6/04* (2006.01)
*F25D 19/00* (2006.01)
*A61B 5/055* (2006.01)

(52) U.S. Cl.
CPC ..... *G01R 33/3804* (2013.01); *G01R 33/3815* (2013.01); *H01F 6/04* (2013.01); *H01F 6/06* (2013.01); *A61B 5/055* (2013.01); *F25D 19/00* (2013.01)

(58) Field of Classification Search
CPC ........ F17C 2270/0536; G01R 33/3856; G01R 33/3804; G01R 33/3403; H01F 6/04; H01F 6/06
USPC ......................................... 62/51.1
See application file for complete search history.

(56) References Cited

U.S. PATENT DOCUMENTS 4,689,970 A 9/1987 Ohguma et al.
5,551,243 A 9/1996 Palkovich et al.
(Continued)

FOREIGN PATENT DOCUMENTS

JP H08159633 A 6/1996
JP 2003336921 A 11/2003
(Continued)

OTHER PUBLICATIONS

Yokoi, JP2011156113Trans (English Translation), Aug. 2011.*
Imai, JP2007143865Trans (English Translation), Jun. 2007.*
GE Healthcare, Optima MR450w, 2010.*

*Primary Examiner* — Justin Jonaitis
*Assistant Examiner* — Eric Ruppert
(74) *Attorney, Agent, or Firm* — Schiff Hardin LLP

(57) ABSTRACT

A magnetic resonance apparatus has a magnet unit that includes at least one superconducting basic magnetic field coil, a magnet housing unit surrounding the at least one superconducting basic magnetic field coil, a cooling system that has at least one cooling loop and a heat absorption unit to cool the at least one superconducting basic magnetic coil, and an additional unit. The cooling system has a switching unit with at least one first cooling mode, and the switching unit couples the at least one cooling loop of the cooling system with the additional unit for a heat exchange in the first cooling mode.

10 Claims, 3 Drawing Sheets

(56) References Cited

U.S. PATENT DOCUMENTS

| | | |
|---|---|---|
| 6,525,537 B2 * | 2/2003 | Nerreter .................. 324/322 |
| 2002/0148604 A1 * | 10/2002 | Emeric et al. ............. 165/206 |
| 2005/0035764 A1 * | 2/2005 | Mantone et al. ........... 324/318 |
| 2006/0266054 A1 * | 11/2006 | Steinbach ............... F25D 16/00 62/79 |
| 2009/0184713 A1 | 7/2009 | Tigwell |
| 2010/0271028 A1 * | 10/2010 | Kawamoto ............. 324/318 |
| 2012/0176134 A1 | 7/2012 | Jiang et al. |
| 2012/0196753 A1 | 8/2012 | Laskaris et al. |
| 2013/0023418 A1 | 1/2013 | Ackermann et al. |
| 2013/0203603 A1 * | 8/2013 | Harrison ............... H01F 6/04 505/162 |
| 2014/0114175 A1 | 4/2014 | Harrison |

FOREIGN PATENT DOCUMENTS

| | | | |
|---|---|---|---|
| JP | 2007143865 | * | 6/2007 |
| JP | 2007143865 A | | 6/2007 |
| JP | 2010267661 A | | 11/2010 |
| JP | 2011110131 A | | 6/2011 |
| JP | 2011156113 | * | 8/2011 |
| JP | 2011156113 A | | 8/2011 |

* cited by examiner

METHOD AND MAGNETIC RESONANCE APPARATUS WITH A COOLING SYSTEM TO COOL A SUPERCONDUCTING BASIC MAGNETIC FIELD COIL

BACKGROUND OF THE INVENTION

Field of the Invention

The present invention concerns a magnetic resonance apparatus with: a magnet unit that has at least one superconducting coil that generates a basic magnetic field, a magnet housing unit surrounding the at least one superconducting coil, a cooling system that has at least one cooling loop, and a heat absorption unit to cool the at least one superconducting basic magnetic coil; and an additional unit.

Description of the Prior Art

Magnetic resonance devices normally have a cooling system with two cooling loops to cool the superconducting that generate the basic magnetic field coils. A first cooling loop thermally couples to a cryostat unit with a helium compressor and a cryo-head that is designed to cool helium at temperatures of approximately −270° C. Waste heat of the cryostat unit is transferred to the first cooling loop. A second cooling loop of the cooling system thermally couples to the first cooling loop so that heat energy of the first cooling loop is transferred to the second cooling loop. It is therefore ensured that the first cooling loop always exhibits an advantageous cooling temperature for cooling the cryostat unit.

If a failure of the second cooling loop now occurs, cooling of the superconducting basic magnetic coil is no longer ensured since this ultimately also leads to an overheating and/or a deactivation of the first cooling loop. The deactivation of the first cooling loop is required in the event of a failure of the second cooling loop, since a transfer of waste heat away from the first cooling loop (and therefore from the cryostat unit) is no longer provided. If the cryostat unit (in particular the helium compressor and the cryo-head) can no longer be operated, this leads to a vaporization of the helium that is present in a helium vessel of the cryostat unit, and therefore increases a helium pressure in the helium vessel. If the helium pressure exceeds a limit value, the helium begins to escape from the helium pressure, such that high costs can occur due to the replacement of helium for the operation of the magnetic resonance apparatus. For example, given a failure of the cooling system, a vaporization rate can encompass approximately 2 l to 3 l of liquid helium per hour.

This problem is especially disadvantageous in magnetic resonance apparatuses with reduced helium fill volumes. In such apparatuses, the fill level of liquid helium within the helium vessel that is required for a safe operation of the magnetic resonance device can already fall below a minimum after only a short duration of a failure of the cooling system.

SUMMARY OF THE INVENTION

An object of the present invention is to provide a cooling system to cool at least one superconducting basic magnetic field coil that continues to ensure cooling of the superconducting basic magnetic coil given a disruption of individual sub-components of the cooling system, thereby maintaining the superconducting capability of the basic magnet.

The invention assumes a magnetic resonance device with: a magnet unit that has at least one superconducting basic magnetic field coil, a magnet housing unit surrounding the at least one superconducting basic magnetic coil, a cooling system that has at least one cooling loop and a heat absorption unit to cool the at least one superconducting basic magnetic coil; and an additional unit.

In accordance with the invention, the cooling system has a switching unit with at least one first cooling mode, the switching unit coupling the at least one cooling loop of the cooling system with the additional unit for heat energy exchange in the first cooling mode. The cooling operation of the superconducting basic magnetic coil and/or of the cooling system can be assisted by the additional unit of the magnetic resonance device. In particular, given a failure and/or a disruption of the heat absorption unit the cooling operation of the superconducting basic magnetic coil and/or of the cooling system can be maintained since heat energy can be passed from the cooling loop to the additional unit. The superconducting capability of the superconducting basic magnetic coil thus can be ensured. The vaporization rate of a cooling fluid (helium, for example) of a cryostat unit for cooling the superconducting basic magnetic coil, can thereby be reduced and/or prevented, particularly during the failure and/or the disruption of the heat absorption unit. The additional unit preferably has at least one sub-component with a high heat capacity and/or a large mass so that an advantageous absorption and/or temporary storage of heat energy within the additional unit can take place, and a failure (in particular of the heat absorption unit) can be compensated in such a manner. The additional unit can be a unit specifically designed for heat energy absorption and/or a unit that performs a conventional functionality within the magnetic resonance device, and only assumes the additional function of heat energy absorption and/or temporary storage in the first cooling mode of the switching unit. In this context, a switching unit is a unit that, depending on a cooling mode, couples the cooling loop with the heat absorption unit and/or with the additional unit with regard to an exchange of heat energy between the cooling loop and the heat absorption unit and/or the additional unit. In a second cooling mode, the cooling loop is advantageously coupled with the heat absorption unit for a heat exchange between said cooling loop and the heat absorption unit. Furthermore, the coupling of the cooling loop with the additional unit is a thermal coupling. The cooling loop of the cooling system is preferably thermally coupled with a cryostat unit of the superconducting basic magnetic coil, wherein the cryostat unit has a helium compressor and/or a cryo-head, in particular a helium cooling loop for cooling the superconducting basic magnetic coil, such that waste heat of the helium cooling loop and/or of the helium compression can be discharged to the additional unit via the cooling loop by the switching unit. The heat absorption unit can include a second cooling loop that is designed to be separate from the at least one cooling loop, and/or can include a heat absorption unit that can be at least partially integrated into the at least one cooling loop, for example a heat exchanger unit that emits heat energy of the cooling loop to an environment (such as ambient air).

Furthermore, the switching unit has at least two cooling modes, and the selection of a cooling mode of the switching unit is dependent on an operating state of the heat absorption unit. A redundant cooling system to cool and/or to dissipate heat energy of the cryostat unit—in particular of the helium loop—of the superconducting basic magnetic coil is thereby achieved. For example, an operating state of the heat absorption unit can include a normal cooling state of the heat absorption unit or a fault state of the heat absorption unit. In the normal cooling state of the heat absorption unit, heat energy is transferred and/or discharged (via a heat exchanger, for example) from the cooling loop to the heat absorption unit (in particular to a cooling medium, for example ambient air) of the heat absorption unit. In the fault state of the heat absorption unit, a failure and/or disruption of the heat absorption unit exists so that an exchange of heat energy from the cooling loop to the heat absorption unit is prevented.

For example, if the operating state of the heat absorption unit includes a fault state of the heat absorption unit, cooling can be maintained via the first cooling mode of the switching unit and emission of the heat energy to the additional unit, and therefore operation of the superconducting basic magnetic coil can be maintained in spite of the fault state of the heat absorption unit. In particular, the failure of the heat absorption unit can be bridged (bypassed), and therefore the superconducting capability of the basic magnetic coil is maintained.

In a further embodiment of the invention, the heat absorption unit includes a second cooling loop, so the heat absorption unit can be decoupled from the at least one cooling loop of the cooling system. The second cooling loop couples with the at least one cooling loop of the cooling system via a heat exchanger unit.

In an embodiment of the invention, the cooling system has a cryostat unit that is designed to cool a cooling fluid of the superconducting basic magnetic coil, and in the first cooling mode the cryostat unit can be switched into a safety operating state by the switching unit. The amount of heat energy that is created by the cooling of the cooling fluid by the cryostat unit thus can be minimized since, in the safety operating state, the cryostat unit will (for example) still generate only a minimum of a cooling power that is required for an operation of the superconducting basic magnetic coil. The operation of the superconducting basic magnetic coil can additionally be maintained and/or bridged over a longer time period in which the heat absorption unit is in a fault state, for example, wherein the time period to be bridged in the fault state can be up to several hours. For example, the safety operating state of the cryostat unit can include a standby operating state, and/or a pulsed operating state in which an active mode (in which a cooling power is generated to cool the helium) and a non-active mode (in which no cooling power is generated) of the cryostat unit alternate.

A structurally simple thermal coupling of the additional unit with the first cooling loop can be achieved when the cooling system has at least one valve unit, the valve unit being controllable by the switching unit. The valve unit—in particular individual valves of the valve unit—can be controlled depending on the cooling mode of the switching unit, so that in the fault state of the heat absorption unit the cooling loop of the cooling system can be varied such that it can thermally couple with the additional unit.

In a further embodiment of the invention, the cooling system has a temperature sensor unit to detect the cooling temperature. The temperature of the additional unit (in particular the heat energy storage of the additional unit) can therefore be detected. The cooling temperature is transmitted and/or relayed from the temperature sensor unit to the switching unit so that monitoring and/or supervision of the cooling temperature by the switching unit can always take place.

The switching unit can be designed to thermally decouple the additional unit from the first cooling loop upon the cooling temperature exceeding a threshold, so protection of the additional unit can be achieved. The additional unit thus can be protected against overheating, which is advantageous in the case of an additional unit that is an existing unit of the magnetic resonance device (for example a gradient coil unit and/or an electronic unit, etc.) with functionality other than heat energy storage.

Furthermore, the additional unit can be designed independently of the heat absorption unit, with the additional unit being used for heat energy storage (in particular given a fault state of the heat absorption unit) so that a heat reservoir is always available for storage of the waste heat of the cryostat unit.

The additional unit preferably is an existing unit that is already present within the magnetic resonance device, so the additional unit has an additional functionality (in addition to storage of heat energy) in the operation of the magnetic resonance device. A particularly compact and cost-saving additional unit thus is provided for intermediate storage of heat energy.

As is used, the magnet unit includes a gradient control unit, and when the additional unit is formed at least in part by the gradient coil unit, the cooling system can be integrated within the magnetic resonance device (in particular within the magnet unit) in a particularly compact and cost-saving manner. In accordance with the invention, an already existing unit of the magnetic resonance device, with the functionality other than heat storage and/or energy storage (for example, the functionality of generating gradient pulses) is used as a heat energy storage to bridge a disruption of the heat absorption unit. The gradient coil unit is preferably made of a cupric material and a fiberglass-reinforced material, wherein the cupric material has a specific heat capacity of approximately 0.35 kJ/kgK, and the fiberglass-reinforced material has a specific heat capacity of approximately 1.1 kJ/kgK. Given a mass of approximately 500 kg of the gradient coil unit, after a coupling time of approximately 1 hour with the cooling loop of the cooling system with a heating power of approximately 6 kW of the cryostat unit, the gradient coil unit could exhibit a temperature increase of approximately 60 K, for example.

It is also usual for the magnetic resonance device to have an electronic unit, and in another embodiment of the invention, the additional unit is formed at least in part by the electronic unit, so the cooling system can likewise be integrated within the magnetic resonance device in a particularly compact and cost-saving manner. Again, an existing unit of the magnetic resonance, device that has a functionality other than heat storage and/or energy storage, can be used to bridge a disruption of the heat absorption unit. The electronic unit can hereby have a separate cooling loop with a cooling fluid to cool individual electronic components, and this separate cooling loop can be thermally coupled by the switching unit with the cooling loop of the cooling system in the event of a fault of the heat absorption unit. The cooling fluid preferably is water, which has a specific heat capacity of approximately 4 kJ/kgK. Given an assumed weight of 500 kg water (corresponding to the gradient control unit) and a heating power of the cryostat unit of approximately 6 kW, only a temperature increase of approximately 10 K is to be expected after one hour.

Furthermore, the additional unit can be formed at least in part by the external housing of the superconducting basic magnetic field coil and/or additional units of the magnet unit and/or the magnetic resonance apparatus that are considered to be reasonable to the those skilled in the art after being informed of the above-described insight that is the basis of the invention.

A particularly advantageous dissipation of heat energy from the first cooling loop can be achieved in an embodiment wherein the additional unit is formed at least in part by a unit specifically designed for heat storage and/or energy storage. For example, the additional unit can be a paraffin storage unit that has an enthalpy of fusion of approximately 200 kF/kg. In further to this, additional external units for storage and/or absorption of heat energy from the cooling system of the magnetic resonance device that appear to be reasonable to those skilled in the art are conceivable, for example energy storage units and/or heat storage units that are already installed within a building in which the magnetic resonance device is installed and/or within a heating system.

Furthermore, the invention encompasses a method to cool a superconducting basic magnetic coil of a magnetic resonance device, wherein a fault state of a heat absorption unit of a cooling system causes a switching unit to switch to a first cooling mode, and in this first cooling mode a cooling loop of the cooling system is thermally coupled with an additional unit. The cooling operation of the superconducting basic magnetic coil and/or the cooling system thus can be supported by the additional unit of the magnetic resonance device. In particular, given a failure and/or a disruption of the heat absorption unit, the cooling operation of the superconducting basic magnetic coil and/or of the cooling system thus can be maintained since heat energy can be discharged from the cooling loop of the cooling system to the additional unit. In particular, it can be ensured in this manner that no loss of the superconducting capability of the superconducting basic magnetic coil (i.e., a quench) occurs. The vaporization rate of the cooling fluid (helium, for example) of the cryostat unit to cool the superconducting basic magnetic coil can advantageously be reduced and/or prevented, particularly during the failure and/or disruption of the heat absorption unit.

In a further embodiment of the method, the cryostat unit of the cooling system is operated in a safety operating state in the first cooling mode of the switching unit. The amount of heat energy that is created upon cooling of the cooling fluid by means of the cryostat unit can therefore be minimized because, for example, in the safety operating state the cryostat unit will generate only a minimum of cooling power that is required for the operation of the superconducting basic magnetic coil. In addition to this, the operation of the superconducting basic magnetic coil can advantageously be maintained and/or bridged over a long time period in which (for example) the heat absorption unit is in a fault state. The time period to be bridged in the fault state can be up to several hours, for example. The safety operating state of the cryostat unit can include a pulsed operating state, for example.

In an embodiment, the cooling temperature of the additional unit is monitored in the first cooling mode. The additional unit thus can be protected against overheating, as this is advantageous particularly if the additional unit at least partially is a unit that is integrated within the magnet unit and/or the magnetic resonance device that, in addition to a function of heat energy absorption, also has another functionality for regular operation (normal) of the magnet unit and/or of the magnetic resonance device.

DESCRIPTION OF THE PREFERRED EMBODIMENTS

Figure 1:
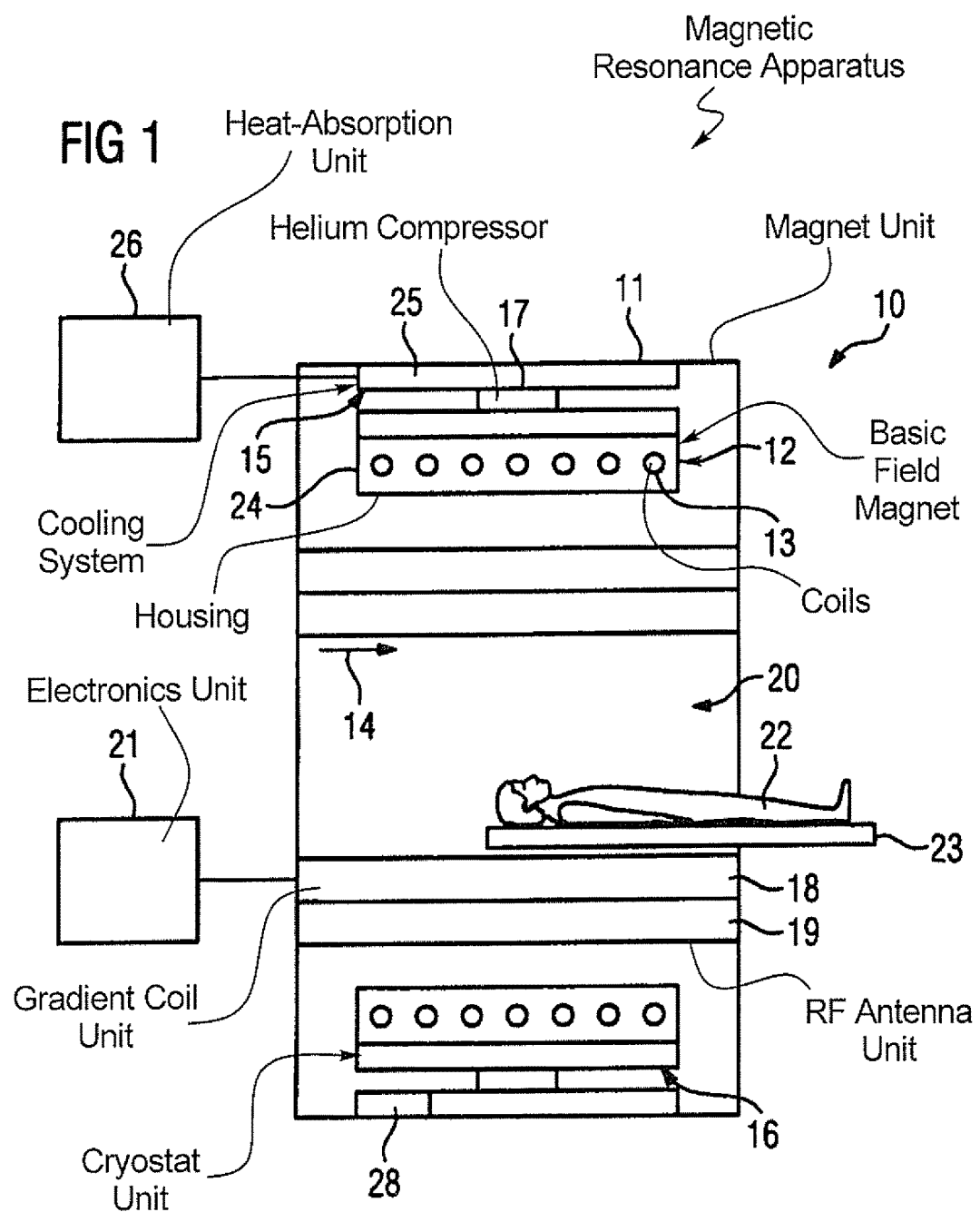
FIG. 1 schematically illustrates a magnetic resonance apparatus according to the invention.

A magnetic resonance apparatus 10 according to the invention is schematically depicted in FIG. 1. The magnetic resonance apparatus 10 includes a magnet unit 11 with a basic field magnet 12 that has a superconducting basic magnetic field coil 13, or multiple superconducting basic magnetic field coils 13, to generate a strong (and in particular constant) basic magnetic field 14.

For operation of the magnetic resonance apparatus 10, it is necessary that the one superconducting basic magnetic field coil 13 or the multiple superconducting basic magnetic field coils 13 be cooled with a cooling fluid (liquid helium) to a temperature of approximately −270° C. For this purpose, the magnetic resonance apparatus 10—in particular the magnet unit 11—has a cooling system 15 with a cryostat unit 16. The cryostat unit 16 includes a helium compressor 17 and a cryo-head (not shown in detail) to cool the helium. The superconducting basic magnetic coil 13 is externally shielded by a magnet housing unit 24.

Furthermore, the magnet unit 11 has a gradient coil unit 18 to generate magnetic field gradients of MR signals for a spatial coding during a data acquisition procedure for imaging. Furthermore, the magnet unit 11 has a radio-frequency (RF) antenna unit 19 that is operated to radiate RF energy that deflects (excites) nuclear spins in a subject from the polarized state that arises in the basic magnetic field 14 generated by the basic field magnet 12. The radio-frequency antenna unit 19 radiates radio-frequency pulses in a magnetic resonance data acquisition sequence into an examination space that is essentially formed by a patient accommodation region 20. Furthermore, the magnetic resonance apparatus 10 has an electronic unit 21 that is designed to control the gradient coil unit 18 and to control the radio-frequency antenna unit 19.

The (usually cylindrical) patient accommodation region 20 accommodates a patient 22, the patient accommodation region 20 being cylindrically enclosed in a circumferential direction of the magnet unit 11. The patient 22 can be moved into the patient accommodation region 20 by a patient support device 23 of the magnetic resonance apparatus 10. This patient support device 23 has a bed table that is arranged so as to be movable within the magnetic resonance apparatus 10.

To discharge waste heat of the cryostat unit 16, the cooling system 15 has a cooling loop 25 (that is formed by a first cooling loop) and a heat absorption unit 26, wherein the heat absorption unit 26 forming a second cooling loop. The first cooling loop 25 is coupled with the cryostat unit 16 in terms of heat exchange in order to dissipate waste heat of the cryo-head and/or of the helium compressor 17 during the generation of cooling power. For this purpose, the first cooling loop 25 has cooling lines in which the cooling fluid circulates. For example, the cooling fluid can be formed by water and/or by additional fluids that are considered to be reasonable to those skilled in the art. The second cooling loop is coupled via heat exchanger unit 27 with the first cooling loop 25 with regard to a heat exchange, such that heat energy from the first cooling loop 25 can be discharged into the second cooling loop, and therefore an effective cooling of the cryostat unit 16 is always ensured. The heat exchanger unit 27 can hereby be arranged within the first cooling loop 25 and/or the second cooling loop. Alternatively, the heat exchanger unit can be designed as separate from the first cooling loop 25 and the second cooling loop.

The cooling system 15 furthermore has a switching unit 28. The switching unit 28 can be switched to different switch states that respectively set or designate multiple cooling modes. Selection of a cooling mode within the switching unit 28 is made depending on an operating state of the heat exchanger unit 26, in particular on an operating state of the second cooling loop. For this purpose, the switching unit 28 is coupled (in communication) with the second cooling loop so as to allow detection of the operating state of the second cooling loop.

The operating state of the second cooling loop can include a fault state in which cooling and/or dissipation of heat energy can no longer be ensured by means of the second cooling loop, and/or is prevented. In addition, the fault state can be a state in which a heat exchange of the second cooling loop with the first cooling loop 25 can no longer be ensured. Alternatively or additionally, the fault state of the second cooling loop can include a fault of the heat exchanger unit 27. An additional operating state of the second cooling loop can be a normal cooling operating state, for example, in which the second cooling loop exhibits no fault, and heat energy exchange takes place between the first cooling loop 25 and the second cooling loop.

If the second cooling loop is in the operating state defined as the fault state, a first cooling mode is selected within the switching unit 28. In contrast to this, if the second cooling loop is in a normal cooling operating state, a second cooling mode is selected within the switching unit 28. In this second cooling mode, the second cooling loop 26 is thermally coupled with the first cooling loop 25 by the switching unit 28 with regard to exchange of heat energy.

The detection of the operating state of the second cooling loop and the selection of a corresponding cooling mode within the switching unit 28 take place automatically and/or independently within the switching unit 28. For this purpose, the switching unit 28 has appropriate software and/or computer programs that are stored within a memory unit of the switching unit 28, so as to execute and/or initiate steps to detect an operating state of the second cooling loop and/or to select a corresponding cooling mode at a processor during a workflow.

In the first cooling mode of the switching unit 28, coupling of the first cooling loop 25 with the additional unit 29 (which is a component of the magnetic resonance apparatus 10) with regard to exchange of heat energy is performed by the switching unit 28. The additional unit 29 is designed independently of the second cooling loop of the cooling system 15, such that a heat energy of the first cooling loop 25 can be transferred to the additional unit 29 given a fault of the second cooling loop, and therefore operation of the magnet unit 11 can be maintained in spite of the fault state of the second cooling loop.

The cooling system 15 furthermore has a valve unit 30 with multiple valves. The individual valves of the valve unit 30 are controllable by the switching unit 28. In the first cooling mode of the switching unit 28, all valves that are situated within the first cooling loop 25, are switched by switching unit 28 such that cooling lines within the first cooling loop 25 form a closed loop that includes both a circulation pump (not shown in detail) of the first cooling loop 25 and a heat exchanger unit with the cryostat unit 16. This state of the valve unit 30—in particular the respective states of the individual valves—also enables a coupling (in particular a thermal coupling) of the closed loop with the additional unit 29.

Furthermore, in the first cooling mode of the switching unit 28 the cryostat unit 16 is switched by the switching unit 28 into a safety operating state. For example, the safety operating state can be a pulsed operating state, in which only the amount of cooling capacity that is necessary to directly prevent vaporization and/or escape of helium is generated within the cryostat unit 16. As an alternative, additional components of the cooling system 15 and/or the magnet unit 11 can be switched by the switching unit 28 into a standby mode, such that an additional generation of heat energy is advantageously prevented.

The additional unit 29 preferably is a unit with a high mass and a significant heat storage capacity. For example, the additional unit 29 can be the gradient coil unit 18 and/or a housing of the magnet unit 11 and/or the electronic unit 21, in particular a cooling loop (not shown in detail) of the electronic unit 21, and/or additional units that are considered to be reasonable to those skilled in the art after being informed of the basis of the invention.

Figure 2:
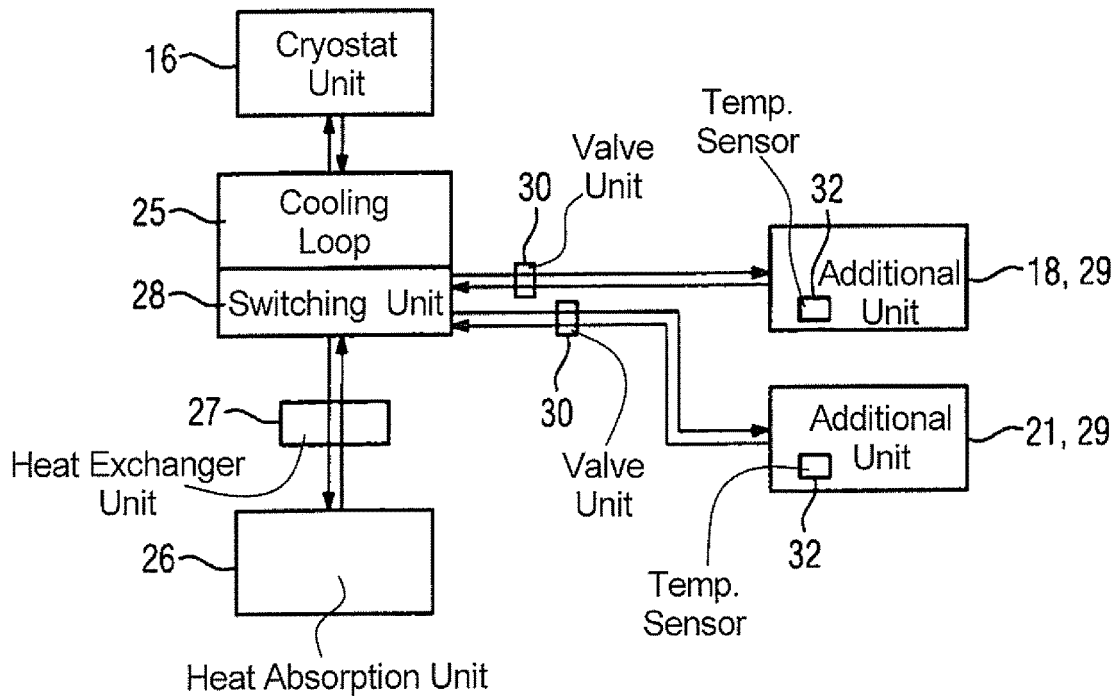
FIG. 2 shows a first exemplary embodiment of a cooling system of the magnetic resonance device, in a schematic presentation.

In the exemplary embodiment of FIG. 2, the additional unit 29 is or includes the gradient coil unit 18. The gradient coil unit 18 is preferably made of a cupric material and a fiberglass-reinforced material, wherein the cupric material has a specific heat capacity of approximately 0.35 kJ/kgK and the fiberglass-reinforced material has a specific heat capacity of approximately 1.1 kJ/kgK. Given a mass of approximately 500 kg of the gradient coil unit 18, the gradient coil unit 18 can exhibit a temperature increase of approximately 60 K after approximately 1 hour given a heating power of the cryostat unit 16 of approximately 6 kW.

Furthermore, in the exemplary embodiment of FIG. 2, the additional unit 29 at least in part includes the electronic unit 21, in particular an existing cooling loop of the electronic unit 21 that is fashioned to be separate from the cooling system 15 of the superconducting basic magnetic coil 13. The cooling loop of the electronic unit 21 that is fashioned to be separate from the cooling system 15 of the superconducting basic magnetic coil 13 has a cooling fluid to cool individual electronic components of the electronic unit 21. In the exemplary embodiment, the cooling fluid is water, which has a specific heat capacity of approximately 4 kJ/kgK. Given a heating power of approximately 6 KW of the cryostat unit 16 (which is identical to that of the gradient control unit 18) and an identically assumed mass of the cooling fluid of approximately 500 kg, after approximately one hour only a temperature increase of approximately 10 K would be expected.

The cooling system 15 also has a temperature sensor 32 that is designed to detect a cooling temperature within the additional unit 29. The temperature sensor 32 is arranged within the additional unit 29. The cooling temperature detected by the temperature sensor 32 is evaluated by the switching unit 28. If the detected cooling temperature hereby exceeds a predetermined threshold, the thermal coupling between the first cooling loop 25 and the additional unit 29 is decoupled by the switching unit 28, and therefore heat energy exchange of the first cooling loop 25 with the additional unit 29 is stopped in order to prevent an overheating of the additional unit 29. For this purpose, the individual valves of the valve unit 30 are also switched and/or brought into the corresponding valve position by the switching unit 28.

The threshold is stored within the switching unit 28, for which the switching unit 28 has a memory unit (not shown in detail). The threshold is dependent on the design of the additional unit 29, in particular dependent on the additional functionality of the additional unit 29. Given multiple available additional units 29, each of these can also have respective different thresholds associated therewith for use in monitoring the cooling temperature by the switching unit 28.

The switching unit 28 is connected with via a data exchange unit (not shown in detail) with the temperature sensor unit 32, the valve unit 30 (in particular the individual valves of the valve unit 30) and/or additional units or components of the cooling system 15. The data exchange unit can be a wireless and/or wired data exchange unit and/or additional data exchange units that are considered to be reasonable to those skilled in the art.

As an alternative to FIG. 2, the additional unit 29 can be only a single unit that has the gradient coil unit 18 or the electronic unit 21 or an additional unit of the magnetic resonance apparatus 10 that is considered to be reasonable to those skilled in the art. The single unit is provided for coupling with the first cooling loop 25 in a fault state of the second cooling loop.

Figure 3:
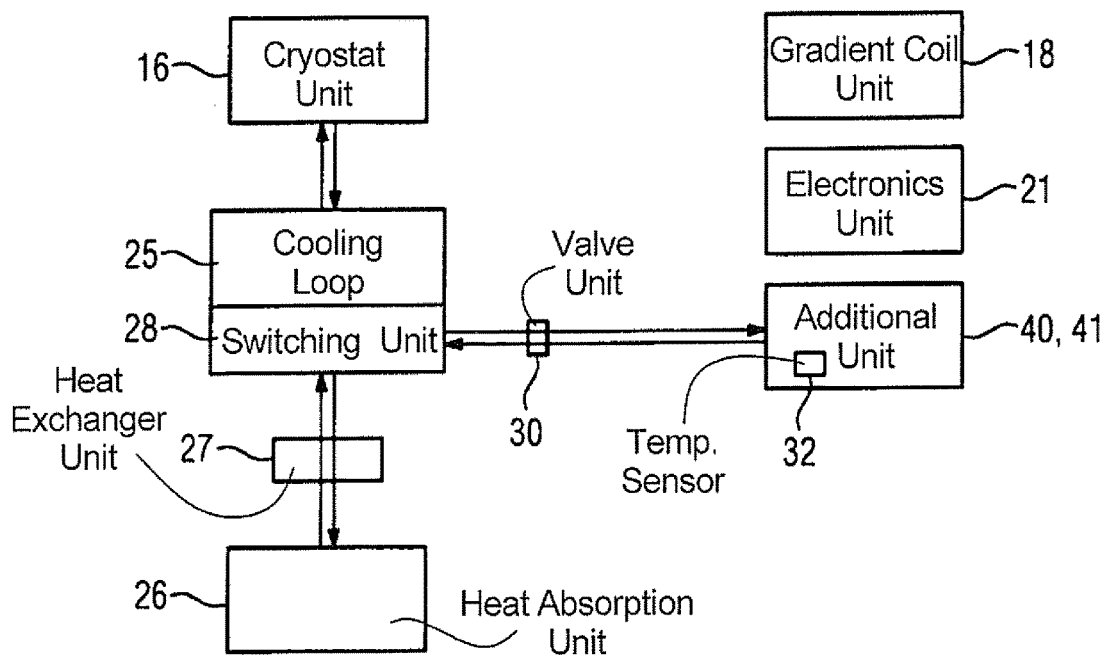
FIG. 3 shows a second exemplary embodiment of a cooling system of the magnetic resonance device, in a schematic presentation.

An alternative exemplary embodiment of the magnetic resonance apparatus 10 is shown in FIG. 3. Modules, features and functions that are in principle the same as in FIGS. 1 and 2 labeled with the same reference characters in FIG. 3. The following description is essentially limited to the differences in FIG. 3 compared to the exemplary embodiment in FIGS. 1 and 2, and the description of the exemplary embodiment in FIGS. 1 and 2 is referenced with regard to modules, features and functions that remain the same.

A magnetic resonance apparatus 10 with a cooling system 15 and an additional unit 40 is presented in FIG. 3. The cooling system 15 in FIG. 3 essentially corresponds to that described with regard to FIG. 2. In contrast to this, however, the additional unit 40 is an energy storage unit 41 that is designed exclusively to store heat energy. The additional unit 40 is a paraffin storage. Paraffin has an enthalpy of fusion of approximately 200 kF/kg., for example, given a heating power of approximately 6 KW of the cryostat unit 16 and an assumed mass of approximately 500 kg, the paraffin storage unit can absorb approximately 4.6 hours of heat energy from the first cooling loop 25 without the paraffin being hereby significantly heated.

Furthermore, the additional unit 40 can include additional energy storage units 41 that are considered to be reasonable to those skilled in the art, for example energy storage units that are already integrated into a heating loop and/or heat storage units of a building in which the magnetic resonance apparatus 10 is installed, etc.

Figure 4:
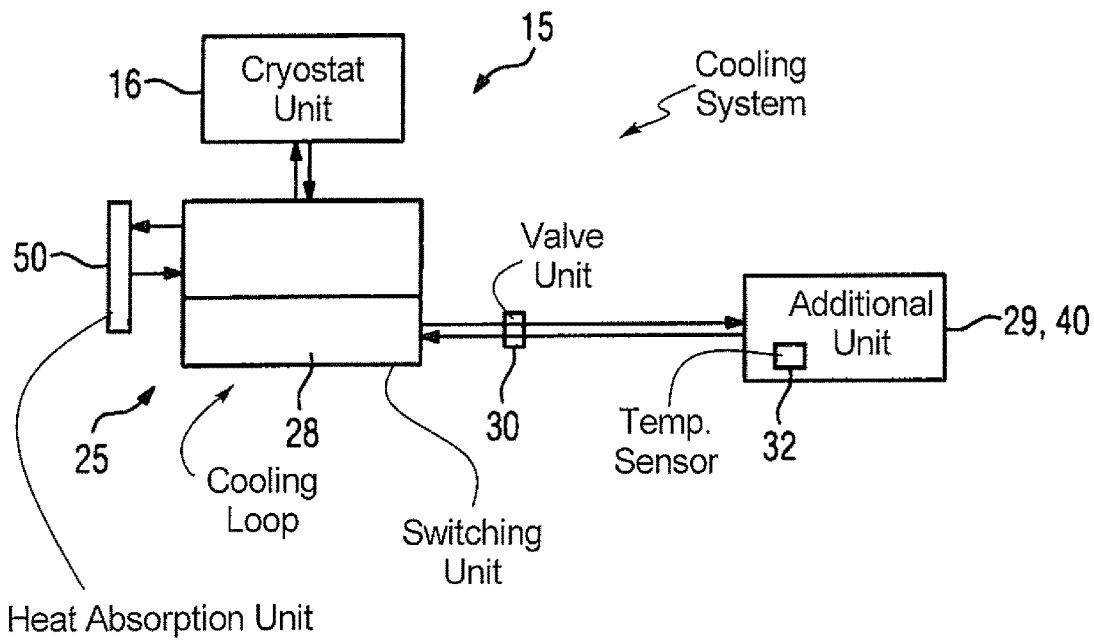
FIG. 4 shows a third exemplary embodiment of a cooling system of the magnetic resonance device, in a schematic presentation.

An alternative exemplary embodiment of the magnetic resonance apparatus 10 is shown in FIG. 4. Modules, features and functions that remain essentially the same as described above are in principle labeled with the same reference characters. The subsequent description is essentially limited to the differences relative to the exemplary embodiments in FIGS. 1 through 3, and the description of the exemplary embodiments in FIG. 1 through 3 is referenced with regard to modules, features and functions that remain the same.

A cooling system 15 of a magnetic resonance apparatus 10 with a heat absorption unit 50 of an alternative design relative to that of FIGS. 2 and 3 is schematically described in FIG. 4. The heat absorption unit 50 is integrated within a first cooling loop 25, wherein the cooling system 15 has only a single cooling loop 25 in addition to the cryostat unit 16. In the present exemplary embodiment, the heat absorption unit 50 comprises a heat exchanger unit (not shown in detail) that outputs a heat energy of the first cooling loop 25 to an environment (for example to the air) and therefore produces a cooling of the first cooling loop 25.

In a fault state of the heat absorption unit 50 or in the first cooling mode of the switching unit 28, all valves that are arranged within the first cooling loop 25 are switched by the switching unit 28 such that cooling lines within the first cooling loop 25 form a closed loop, wherein the closed loop enables a coupling (in particular a thermal coupling) with the additional unit 29, 40. In addition, the individual valves of the valve unit 30 are switched such that the heat absorption unit 50 is decoupled (in particular is thermally decoupled) from the first cooling loop 25.

In the present exemplary embodiment, the additional unit 29, 40 can be designed according to the additional units 29 in the embodiments of FIG. 2 and/or according to the additional unit 40 in the embodiments of FIG. 3. It is also conceivable for a thermal coupling of the first cooling loop 25 with multiple additional units 29, 40 to take place in the first cooling mode by means of the switching unit.

Figure 5:
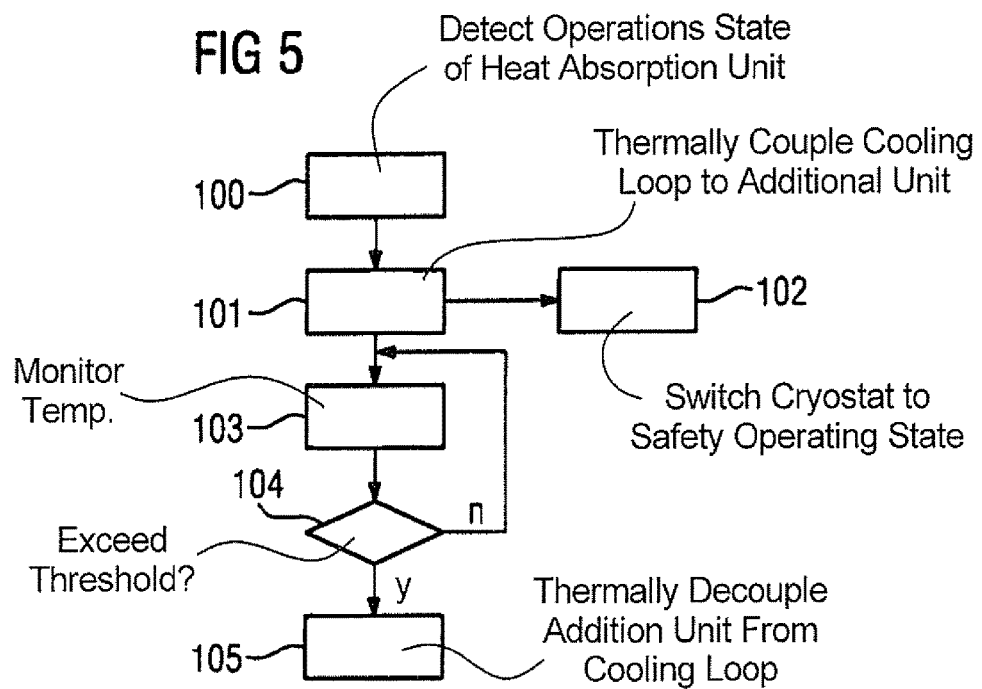
FIG. 5 is a flowchart of the basic steps of the method according to the invention for cooling a superconducting basic magnetic field coil.

A method according to the invention for the cooling of a superconducting basic magnetic coil 13 or multiple superconducting basic magnetic coils 13 is schematically presented in FIG. 5. In a first method step 100, an operating state of the heat absorption unit 26, 50 is detected by the switching unit 28. If this operating state includes a fault state of the heat absorption unit 26, 50, within the switching unit 28 the first cooling mode is selected from multiple available cooling modes. In the first cooling mode, in the further method step 101 a thermal coupling of the first cooling loop 25 with the additional unit 29, 40 by the switching unit 28 takes place so that a heat energy is passed from the first cooling loop 25 to the additional unit 29, 40. In the additional method step 101, the individual values of the valve unit 30 are hereby controlled and switched by the switching unit 28 such that the first cooling loop 25 thermally couples with the additional unit 29, 40.

The heat absorption unit 26, 50 and the additional unit 29, 40 are designed according to the statements regarding FIG. 1 through 4.

In the first cooling mode of the switching unit 28, in an additional method step 102 the cryostat unit 16 is additionally switched by the switching unit 28 into a safety operating state. For example, the safety operating state can include a pulsed operating state in which only the amount of cooling power that directly prevents vaporization and/or escape of helium is generated within the cryostat unit 16.

In a further method step 103, a temperature (in particular a cooling temperature) of the additional unit 29, 40 is detected and monitored by the switching unit 28 together with the temperature sensor unit 32. For this purpose, the cooling temperature is compared by the switching unit 28 with the threshold in an additional method step 104. The method step 104 is formed by a query that is executed within the switching unit. A query is hereby made by the switching unit as to whether the detected cooling temperature of the additional unit 29, 40 exceeds the threshold. If the detected cooling temperature exceeds the threshold, in an additional method step 105 the additional unit 29, 40 is thermally decoupled from the switching unit 28 by the first cooling loop 25 so that an overheating of and/or a damage to the additional unit 29, 40 is prevented.

By contrast, if the detected cooling temperature of the additional unit 29, 40 is below the threshold, a cooling temperature continues to be detected by the temperature sensor unit 32 and this cooling temperature is monitored by the switching unit 28 in the method steps 103, 104, 105.

In an embodiment of the method according to the invention, the switching unit 28 includes a software and computer programs required for the above-described operation that are stored in a memory unit (not shown in detail) of the switching unit 28. In addition to this, the switching unit 28 has a processor to execute the required software and computer programs.

Although modifications and changes may be suggested by those skilled in the art, it is the intention of the inventor to embody within the patent warranted hereon all changes and modifications as reasonably and properly come within the scope of his contribution to the art.

We claim:

1. A magnetic resonance (MR) apparatus comprising:
    a magnet unit configured to operate to acquire MR data, said magnet unit comprising a basic field magnet having at least one superconducting coil requiring cooling;
    said magnet unit comprising a plurality of additional units each configured to respectively perform an individual operation that participates in the acquisition of said MR data, each individual operation being unrelated to the cooling of said at least one superconducting coil, and at least one of said additional units having a structure that is capable of heat exchange;
    said magnet unit comprising a cooling system that provides said cooling to said at least one superconducting coil, said cooling system comprising a cooling loop in thermal communication with said at least one superconducting coil, and a heat absorption unit that discharges heat from said cooling loop;
    said cooling system comprising a switching unit configured to selectively place said cooling loop in thermal communication with either of said heat absorption unit or said at least one of said additional units that is capable of heat exchange; and
    said switching unit being configured to monitor an operating state of said heat absorption unit to detect a switching-triggering condition in said heat absorption unit and, as long as said switching-triggering condition is not detected, to place said cooling system in a first cooling mode in which said cooling loop is in thermal communication with said heat absorption unit and out of communication with said at least one additional unit and, when said switching-triggering condition is detected, to switch said cooling system to a second cooling mode in which said cooling loop is in thermal communication with both said heat absorption unit and said at least one additional unit, with the heat exchanging capability of said at least one additional unit in said second cooling mode augmenting the discharge of heat from said cooling loop by said heat absorption unit.

2. An MR apparatus as claimed in claim 1 wherein said switching unit is configured to detect an occurrence of a fault state of said heat absorption unit as said switching-triggering condition.

3. An MR apparatus as claimed in claim 2 wherein said cooling is a first cooling loop and wherein said heat absorption unit comprises a second cooling loop, and wherein said switching unit is configured to detect a fault state of said second cooling loop as said fault state of said heat absorption unit.

4. An MR apparatus as claimed in claim 3 wherein said switching unit is configured to thermally decouple said second cooling loop from said first cooling loop upon detection of said fault state of said second cooling loop.

5. An MR apparatus as claimed in claim 2 wherein said cooling system comprises a temperature sensor that detects a temperature within said heat absorption unit, and wherein said switching unit is configured to detect, as said switching-triggering condition, when said temperature in said heat absorption unit detected by said temperature sensor exceeds a predetermined temperature threshold.

6. An MR apparatus as claimed in claim 1 comprising a cryostat configured to cool a cooling fluid that is provided to said cooling loop for cooling said at least one superconducting coil, and wherein said switching unit and said cryostat are configured to place said cryostat in a safety operating state in said second cooling mode.

7. An MR apparatus as claimed in claim 1 comprising a fluid communicating path between said cooling loop and said at least one additional unit, and a valve in said fluid communicating path that is operated by said switching unit, and wherein said switching unit is configured to close said valve in said first cooling mode and to open said valve in said second cooling mode.

8. An MR apparatus as claimed in claim 1 wherein said magnet unit comprises a gradient coil unit, and wherein said at least one additional unit comprises at least a portion of said gradient coil unit.

9. An MR apparatus as claimed in claim 1 wherein said magnet unit comprises a housing, and wherein said at least one additional unit comprises at least a portion of said housing.

10. An MR apparatus as claimed in claim 1 wherein said magnet unit comprises an electronics unit configured to generate control signals that respectively operate said basic field magnet and said plurality of additional units, and wherein said at least one additional unit comprises at least a portion of said electronics unit.

* * * * *